United States Patent [19]
Kovacevic

[11] Patent Number: 5,360,016
[45] Date of Patent: Nov. 1, 1994

[54] FORCE TRANSDUCER FOR A JOINT PROSTHESIS

[75] Inventor: Nebojsa Kovacevic, Plymouth, Minn.

[73] Assignee: N. K. Biotechnical Engineering Company, Minneapolis, Minn.

[21] Appl. No.: 1,048

[22] Filed: Mar. 22, 1993

Related U.S. Application Data

[62] Division of Ser. No. 681,099, Apr. 5, 1991, Pat. No. 5,197,488.

[51] Int. Cl.⁵ ............................................. A61B 5/103
[52] U.S. Cl. ..................................... 128/782; 128/774; 606/102; 73/862.045; 73/862.046; 73/862.632
[58] Field of Search ................. 128/774, 782; 606/90, 606/91, 99, 61, 53, 102; 623/16, 17, 18, 20, 22; 73/862.042, 862.043, 862.044, 862.045, 862.632, 862.633, 862.627, 862.637, 862.636, 862.68, 862.046, 862.541

[56] References Cited

U.S. PATENT DOCUMENTS

| 3,213,400 | 11/1961 | Gieb | 73/862.632 |
| 3,696,317 | 10/1972 | Farr . | |
| 3,915,015 | 10/1975 | Crane et al. | 73/862.044 |
| 3,916,451 | 11/1975 | Buechel et al. | 623/18 |
| 4,051,451 | 9/1977 | Kurtz et al. | 73/862.632 |
| 4,206,517 | 6/1980 | Pappas et al. | 623/18 |
| 4,211,228 | 7/1980 | Cloutier . | |
| 4,267,725 | 5/1981 | Roth et al. . | |
| 4,309,778 | 1/1982 | Buechel et al. . | |
| 4,340,978 | 6/1982 | Buechel et al. . | |
| 4,426,884 | 1/1984 | Polchaninoff . | |
| 4,501,266 | 2/1985 | McDaniel . | |
| 4,503,705 | 3/1985 | Polchaninoff . | |
| 4,573,362 | 3/1986 | Amlani | 73/862.044 |
| 5,619,658 | 10/1986 | Pappas et al. | 623/22 |
| 4,624,674 | 11/1986 | Pappas et al. | 623/22 |
| 4,680,606 | 7/1987 | Knutti et al. | 357/26 |
| 4,712,542 | 12/1987 | Daniel et al. . | |
| 4,763,097 | 8/1988 | Kant et al. . | |
| 4,793,193 | 12/1988 | Borgudd | 73/862.043 |
| 4,795,473 | 1/1989 | Grimes . | |
| 4,804,000 | 2/1989 | Lamb et al. . | |
| 4,808,186 | 2/1989 | Smith . | |
| 4,822,362 | 4/1989 | Walker et al. . | |
| 4,834,057 | 5/1989 | McLeod, Jr. . | |
| 4,836,036 | 6/1989 | Jetter | 73/862.632 |
| 4,932,974 | 6/1990 | Pappas et al. | 623/16 |
| 5,050,618 | 9/1991 | Larsen | 128/774 |
| 5,090,421 | 2/1992 | Wagoner, III | 128/774 |
| 5,158,096 | 10/1992 | Clark et al. | 128/777 |

Primary Examiner—Stephen C. Pellegrino
Assistant Examiner—Guy V. Tucker
Attorney, Agent, or Firm—Westman, Champlin & Kelly

[57] ABSTRACT

A force transducer for a joint prosthesis is disclosed. The transducer includes A f5RUw,V,central body having a plurality of cavities formed therein from a lower surface. Each cavity defines a flexure member. A plate is located on the side opposite the cavities and connect to each flexure member through support posts. The support posts localize three applied to the plate to each flexure member. Force sensing elements attached to each flexure member provide a signal corresponding to the force applied to the flexure member.

9 Claims, 4 Drawing Sheets

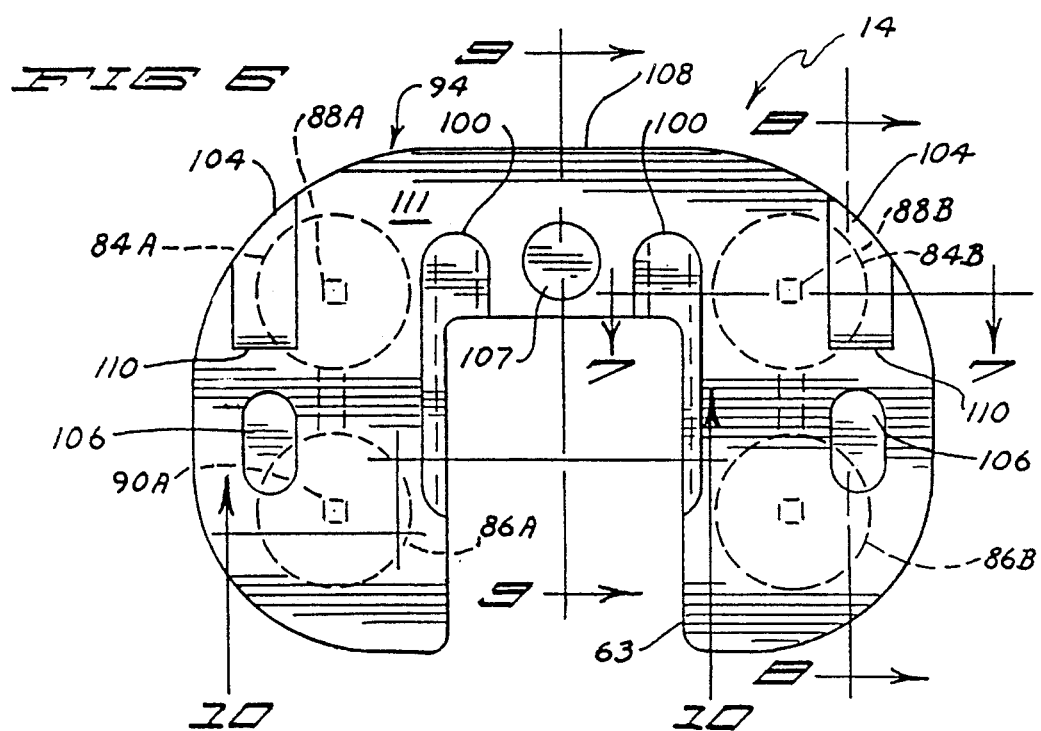
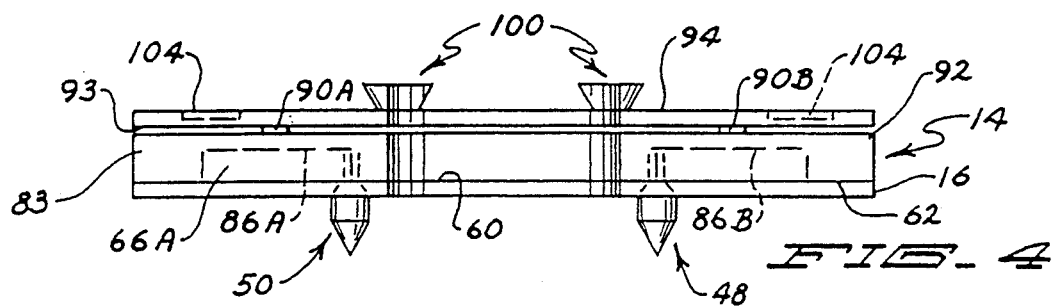
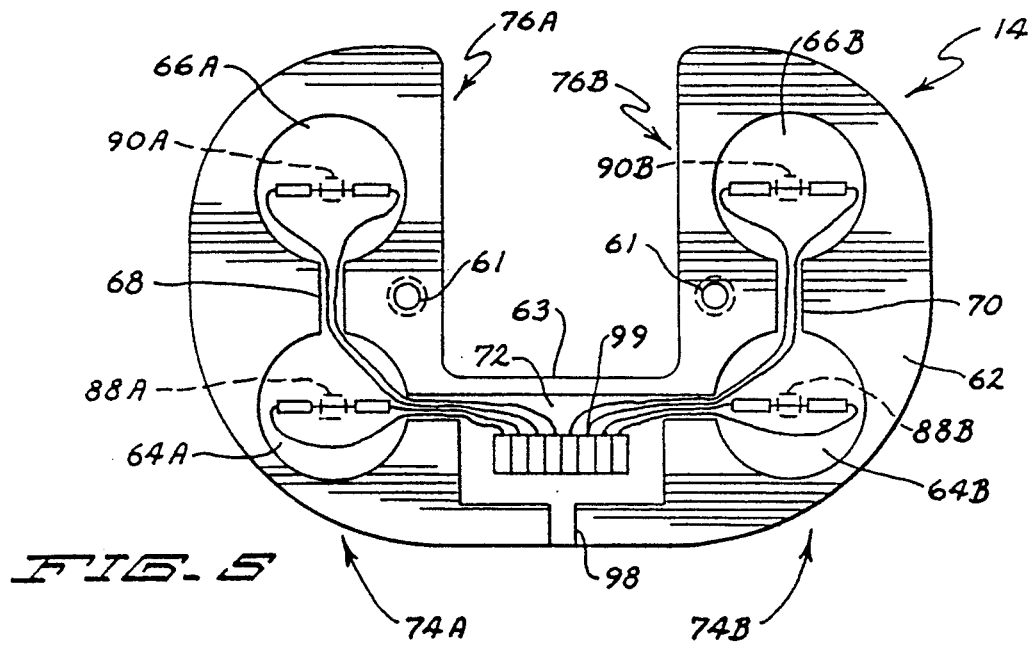

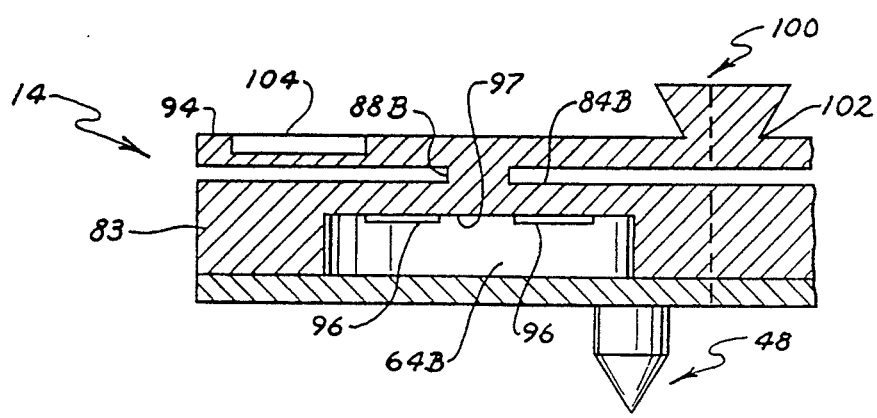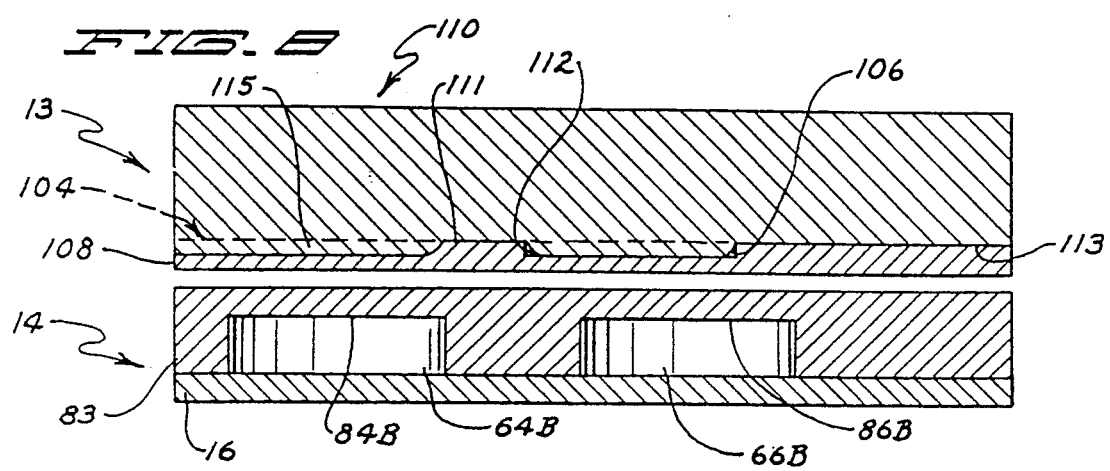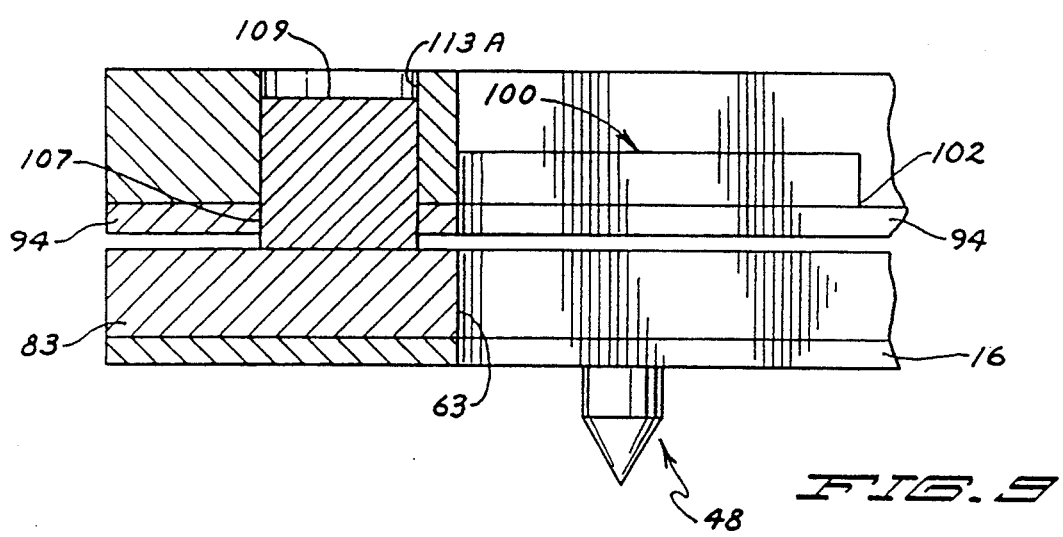

FORCE TRANSDUCER FOR A JOINT PROSTHESIS

This is a divisional of application Ser. No. 07/681,099, filed Apr. 5, 1991 now U.S. Pat. No. 5,197,488.

BACKGROUND OF THE INVENTION

1. Field of the Invention

The present invention pertains generally to a joint prosthesis and, more particularly, to a system that measures forces on a joint prosthesis to determine proper implantation of the prosthesis on a patient.

2. Description of the Prior Art

The human knee is the single largest joint of the human body, but due to its structure, is arguably the most vulnerable to damage. The leg consists principally of a lower bone called a tibia and an upper bone known as the femur. The tibia and femur are hinged together at the knee joint. The knee joint includes femoral condyles supported in an engagement with crescentic fibrocartilages that are positioned on the upper end of the tibia and receive the femur. The joint is held together by numerous ligaments, muscles and tendons. The patella is a similarly supported bone positioned in front of the knee joint and acts as a shield for it.

When the knee joint has been severely damaged from accident, wear, or disease, partial or total knee replacement may be the only viable solution. One type of knee replacement is shown in U.S. Pat. No. 4,340,978 issued to Buechel et al. In this patent, the tibia is resected to form a flat, horizontal platform known as a tibial plateau. The amount of bone structure removed corresponding to the severity of damage to the joint and the necessary allowance needed for the prosthesis. A tibial platform is secured to the tibial plateau with posts or anchors fixed normal or perpendicular to the tibia plateau. The anchors provide additional support to the tibial platform when the joint is subjected to shear, tipping and torque forces present under normal knee articulation.

A femoral component, comprising a curved convex semi-spherical shell, covers the femoral condyles and slidably engages a concave tibial bearing insert. On a side opposite the femoral component, the tibial insert is substantially flat and slidably engages the tibial platform. Interaction of opposing surfaces of these three elements, the femoral component, the tibial insert and the tibial platform allows the prosthesis to function in a manner equivalent to a natural knee joint.

Another tibial platform and a surgical procedure for implantation is described in U.S. Pat. No. 4,822,362 issued to Walker et al.

Crucial to either the complete joint of Buechel et al. or the tibial platform of Walker et al. is proper alignment of the tibial platform on the tibial plateau. Without proper alignment, neither will function correctly whereby uneven forces on the prosthesis may result in excessive contact stresses leading to deformation and/or early wear and thus undesirable short prosthetic life.

Template assemblies have been used in implantation surgical procedures to resect the tibia and align the tibial platform. One such assembly is disclosed in U.S. Pat. No. 4,211,228 issued to Cloutier. This assembly comprises a Y-shaped handle having two flat prongs that are used to check the planes of the resected tibia for overall flatness and to hold temporarily the tibia inserts. An alignment rod, fixed to the flat handle, is aligned visually along the long axis of the tibia, as viewed laterally and anteriorally, to ensure correct positioning of the tibial platform onto the patient's tibia. Since tibial platform alignment does not include movement of the prosthetic components in order to access force loads on the joint, alignment of the tibial platform may not be optimum, realizing pressure differences across the surface of the platform which under normal articulation of the joint may cause fatigue in the prosthesis.

Consequently, there exists a need for a system to dynamically measure and analyze forces present on components of a knee joint prosthesis and all other types of prostheses. The system should measure these forces throughout the normal range of motion of the joint, providing quantitative indications of forces present. The system should be easy to install and yet be removable when the analysis is complete.

SUMMARY OF THE INVENTION

The present invention provides a system for dynamically measuring forces applied to a joint prosthesis. The system comprises a first support member attached to an outer surface of a first bone, a second support member attached to an outer surface of a second bone and a transducer secured to at least one support member and engaging the other support member. The transducer measures forces carried between the first and second support members as the prosthetic joint is articulated and provides representative force output signals at selected locations on at least one of the support members.

The present invention further provides a method for aligning a joint prosthesis between two bones of a patient. The method comprises: locating the force transducer between the two bones; articulating the joint to obtain force measurement data, preferably at spaced locations; collecting the force measurement data; and performing curative steps based on the force measurement data to properly align the joint. In the preferred embodiment, a computer is connected to the transducer to receive or collect the force measurement data. The computer includes a display that presents the data to the operating surgeon in any convenient arrangement such as a graphical, numerical or combined format.

In the preferred embodiment, the transducer comprises a central body having an upper surface and a cavity opening to a lower surface. The cavity defines a flexure member in the body that is responsive to forces applied from the joint prosthesis on the upper and lower surfaces. A strain gauge, such as a resistive strain gauge, is secured to the flexure member to measure the response thereof. To localize forces onto the flexure member, the transducer further includes a support post connected to the flexure member. A second end of the post connects to a plate. Since the plate is separated from the upper surface and receives the forces from one of the support members, the forces are concentrated or localized on the flexure member, increasing the sensitivity of the transducer.

The present invention is particularly useful during the implantation of a knee prosthesis where alignment of the joint prosthesis on the patient is critical to its usefulness. This knee prosthesis comprises a femoral component coupled to a femur; a tibial component that includes a cover plate coupled to a resected tibial plateau with spikes or other forms of anchors; and a tibial platform which slidably engages the femoral component to articulate the joint. A transducer is located between the cover plate and the tibial platform. In the preferred embodiment, the transducer body comprises a plurality of integrally formed spaced apart flexure members, each flexure member defined by a corresponding cavity and defining a force responsive flexure section. Each flexure section provides a corresponding representative force output signal proportional to the forces applied to the flexure member. A plurality of support posts coupled to each flexure member and a plate located above the upper surface localize and distribute the forces applied to the plate. The transducer is secured to the cover plate with threaded portions of the spikes, while the tibial platform slidably mounts to the transducer with a dovetail/notch interconnection. Lateral movement of the platform on the transducer is prevented with protruding elements formed on a lower surface of the transducer cooperating with depressions that function as detents on an upper surface of the plate.

BRIEF DESCRIPTION OF THE DRAWINGS

FIG. 4 is a front plan view of a force transducer mounted on top of the cover plate.

FIG. 5 is a bottom plan view of the force transducer;

FIG. 6 is a top plan view of the force transducer of FIG. 4;

FIG. 7 is a fragmentary sectional view of the force transducer taken along line 7—7 of FIG. 6;

FIG. 8 is a sectional view of the force transducer taken along line 8—8 of FIG. 6 with a tibial platform coupled above;

FIG. 9 is a fragmentary sectional view of the force transducer taken along line 9—9 of FIG. 6 with a tibial platform coupled above;

DETAILED DESCRIPTION OF THE PREFERRED EMBODIMENTS

Figure 1:
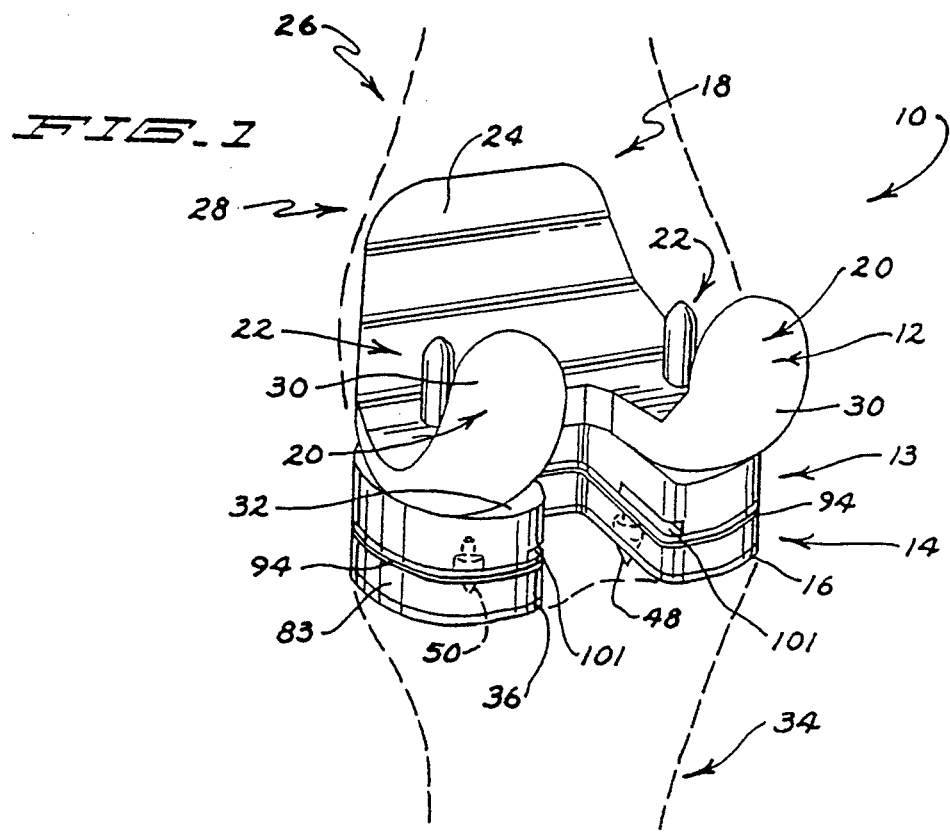
FIG. 1 is a rear perspective view of the present invention comprising a knee prosthesis.

The dynamic force measuring prosthesis of the present invention is shown perspectively as assembly 10 in FIG. 1. Assembly 10 comprises a first support member or femoral component 12, a tibial platform 13, a force transducer 14 and a second support member or tibial cover plate 16 which is formed to transfer loads at selected locations between the tibia and the force transducer. When installed as a replacement assembly for a natural human knee joint, assembly 10 provides quantitative feedback on force load balance across the tibial-femoral joint.

Addressing each component separately, femoral component 12 includes a flange 18 formed integrally with two condyles 20. Femoral component 12 includes a pair of fixing posts or anchors 22 integrally formed on an inside surface 24. Posts 22 are used to fix the femoral component 12 to a femur 26, illustrated only in dotted lines.

An outside (lower) surface 28 of flange 18 provides most of the bearing surface for a patella, not shown, which cooperates with femur 26 to protect the joint. Condyles 20 are provided for replacing the condylar surfaces of femur 26 and include spaced outside bearing surfaces 30.

Immediately below femoral component 12 and in sliding contact with both bearing surfaces 30 is tibial platform 13. Tibial platform 13 includes concave upper bearing surfaces 32, of conventional design, that engages bearing surfaces 30 and support condylar elements 20 of femur 26. In the preferred embodiment, tibial platform 13 comprises a single integrally formed body; however, the present invention will also provide force measurement readings for prostheses incorporating two tibial platforms, one supporting each condyle 20 of femoral component 12.

Tibial transducer 14 and cover plate 16 together provide a stationary mounting structure for assembly 10 on a tibia 34. Cover plate 16 is positioned on a tibia plateau 36 resected by conventional surgical procedures. Plateau 36 is flat and normal to the longitudinal axis of tibia 34.

Figure 3:
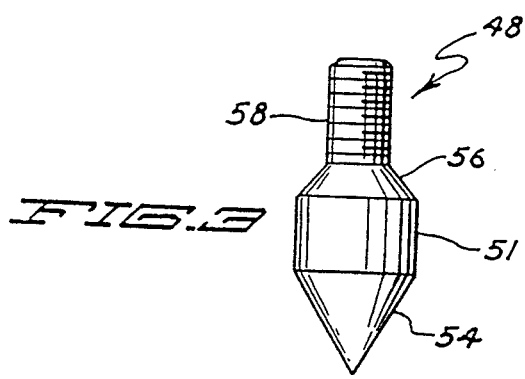
FIG. 3 is an enlarged front plan view of a spike for the knee prosthesis of FIG. 1.
Figure 2:
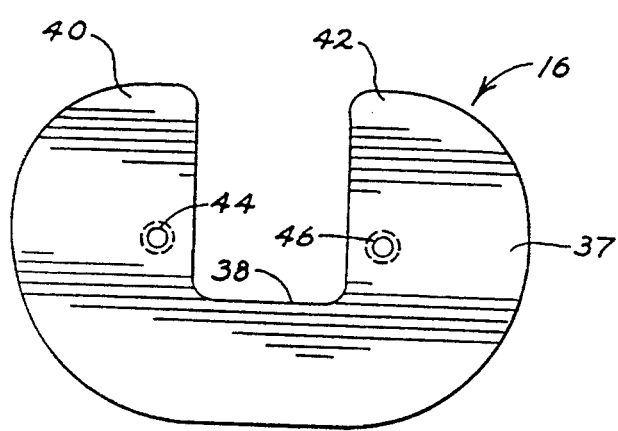
FIG. 2 is a top plan view of a cover plate for the knee prosthesis of FIG. 1.
Figure 10:
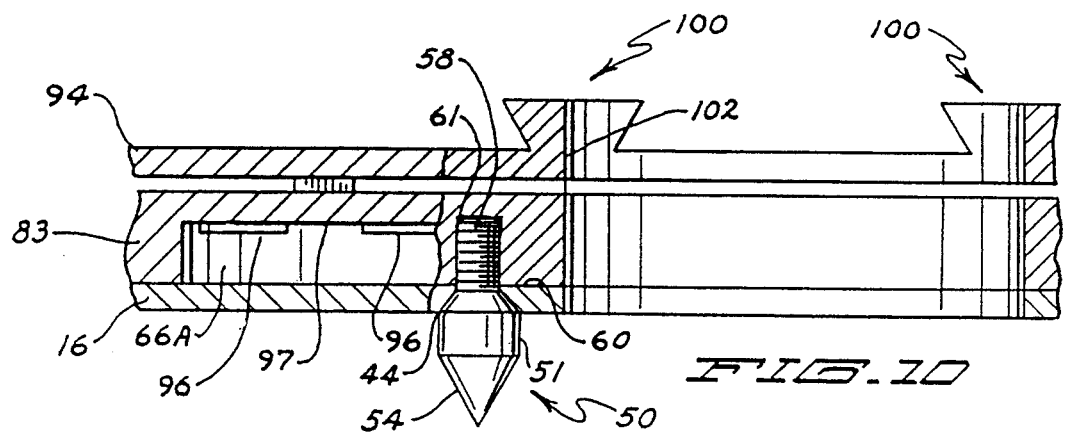
FIG. 10 is a fragmentary sectional view of the force transducer taken along line 10—10 of FIG. 6.

As shown in FIGS. 1 and 2, cover plate 16 comprises a U-shaped support member 37 having a central channel 38. Channel 38 separates two spaced plate sections 40 and 42. Sections 40 and 42 are generally symmetrical with curved, generally circular outer peripheral edges chosen to cover substantially the upper surfaces of tibial plateau 36. Positioned adjacent channel 38 within each plate section 40 and 42 are countersunk apertures 44 and 46. Apertures 44 and 46 receive spikes 48 and 50, which are threaded into transducer 14 and driven into the tibia to align cover plate 16 on plateau 36. Spike 48, shown in detail in FIG. 3, comprises a generally cylindrical body 51 having a downwardly extending conically shaped tip 54. When placed within tibia 34, body 51 and tip 54 extend approximately $\frac{1}{4}$ of an inch below the upper surface of plateau 36 with a countersunk mating surface 56 and threaded stud 58 projecting upwardly. In the preferred embodiment, mating surface 56 cooperates with outwardly extending countersunk inner surfaces of apertures 44 and 46, as shown in FIG. 10. Stud sections 58 hold force transducer 14 on cover plate 16 when inserted through apertures 44 and 46 and threaded into threaded apertures 61 in the lower surface 62 of force transducer 14. Additional spikes or other types of anchors, may be provided if additional support is required to secure cover plate 16 to plateau 36.

As shown in the bottom plan view of FIG. 5, transducer 14 is symmetrically U-shaped having a central channel 63 and two spaced sections overlying the sections 40 and 42 of the cover plate 16. A plurality of cavities 64A, 64B, 66A and 66B defining two anterior force responsive flexure sections 74A and 74B, and two posterior force responsive flexure sections 76A and 76B are formed in the transducer 14. Transducer 14 is constructed from suitable elastic material that is responsive to the forces applied between lower surface 62 and an upper surface 92 on transducer 14, shown in FIG. 4, as assembly 10 is articulated.

Anterior cavities 64A and 64B and posterior cavities 66A and 66B are symmetrically positioned on opposite sides of central channel 63. In the preferred embodiment, each cavity is cylindrical with identical radii, having an opening defined into lower surface 62. Each cavity 64A, 64B, 66A and 66B forms a corresponding thin cylindrical flexure member 84A, 84B, 86A and 86B on central body 83, as shown with hidden lines in FIG. 6 in plain view in FIG. 5, and in section in FIGS. 7, 8 and 10.

A plurality of support posts 88A, 88B, 90A and 90B are secured to an upper surface 92 of central body 83 above cavities 64A, 64B, 66A and 66B, respectively. Support post 88A, 88B, 90A and 90B are further secured to a lower surface 93 of an upper plate 94 having the general U-shaped configuration of cover plate 16 and central body 83. The posts 88A, 88B, 90A and 90B are actually integrally formed between body 83 and upper plate 94 by EDM Machining. Forces applied to upper plate 94 are localized and directed through support posts 88A, 88B, 90A and 90B to the corresponding flexure members 84A, 84B, 86A and 86B. As shown for example in FIG. 7, appropriate strain gauges 96, such as resistive strain gauges, are disposed in each cavity on an inner surface 97 of each flexure member. These strain gauges provide a quantitative response to forces applied between upper plate 94 and cover plate 16. Channels 68 and 70, between adjacent cavities, shown in FIG. 5, provide conduits for electrical leads from strain gauges located in posterior cavities 66A and 66B. Channel 72 provides conduit for all electrical leads of the strain gauges with termination on a suitable connector or terminal strip 99. A channel 98 allows associated leads connected to terminal strip 99 to exit transducer 14.

Although force transducer 14 has been described with particular reference to cavities and flexure members formed therein, other types of forces sensors can be used. Such force sensors include semiconductor or piezo-electric sensors formed within or located on a surface of transducer 14. As with the cavities and flexure members discussed above, these force sensors can be displaced laterally on transducer 14 to provide independent force data for various locations.

Transducer 14 is replaceably attached to tibial platform 13 with upper plate 94. As shown in FIGS. 7, 9 and 10, upper plate 94 includes upwardly extending male dovetails 100 formed symmetrically and longitudinally along a central channel 102 of upper plate 94. Dovetails 100 interlock with corresponding female notches 101 in tibial platform 13 shown in FIG. 1. The interlocking relationship of dovetails 100 and notches 101 aligns transducer 14 with tibial platform 13, preventing slippage laterally between the parts.

Referring to FIGS. 4, 6 and 8, channels 104, depressions 106 and aperture 107 formed in upper plate 94 provide additional alignment and a means for locking transducer 14 to tibial platform 13. As shown in FIG. 6, channels 104 extend parallel to central channel 63 to a anterior periphery edge 108. At an inward or rearward end 110, channels 104 curve upwardly to intersect with an upper surface 111 of upper plate 94.

In line with each of channels 104 are corresponding depressions 106. Protruding elements 112 formed on lower surface 113 of tibial platform 13, after being properly aligned with channels 104, exit channels 104 at rearward end 110 and enter depressions 106. Depressions 106 act as detents for protruding elements 112, preventing tibial platform 13 from releasing and sliding relative to transducer 14. Similar protruding elements 115 engage and remain in channels 104. As shown in FIG. 9, aperture 107 in upper plate 94 aligns with a corresponding aperture 113A in tibial platform 13. A pin 109 is inserted within apertures 107 and 113A to interlock tibial platform 13 to transducer 14.

Although the present invention includes a tibial platform replaceably attached between transducer 13 and femoral component 12, alternative embodiments may increase the height of transducer 13, eliminating tibial platform 4 such that transducer 13 directly engages femoral component 12. The thickness of the components 15. can be adjusted for proper fit and comfort.

Use of transducer 14 ensures proper alignment of assembly 10 on the patient. With proper incisions made surrounding the knee joint, femoral component 12 is secured to the patient's femur and the tibia is resected with conventional osteotomy surgical procedures. Force transducer 14 is then attached to tibial platform 13 with protruding elements 115 and 112 interacting with channel 104 and depressions 106, discussed above. Cover plate 16 is secured to transducer 14 with threaded stud portions 58 of spikes 48 and 50. The conical tips and cylindrical bodies of spikes 48 and 50 are then positioned within appropriate apertures drilled normal to the resected tibial plateau.

With all components properly positioned, the knee joint prosthesis is articulated. Forces transferred down the knee joint prosthesis are detected by the strain gauges located within the cavities formed in transducer 14, as discussed above. Electrical signals representative of these applied forces in four separated locations, are then amplified, conditioned, and presented as quantitative data to the surgeon. By monitoring this data, the surgeon determines if balanced loads exist on the prosthetic joint for the partial or full range of articulation. Unequal forces at the four sensing locations can be noted directly, and the total load or force also can be determined. Load inequality from side to side and front to back is determined. If proper force or load distribution is not present, the surgeon can perform curative steps such as additional partial resection of the tibia to make it flat, or at a slightly different angle.

Figure 11:
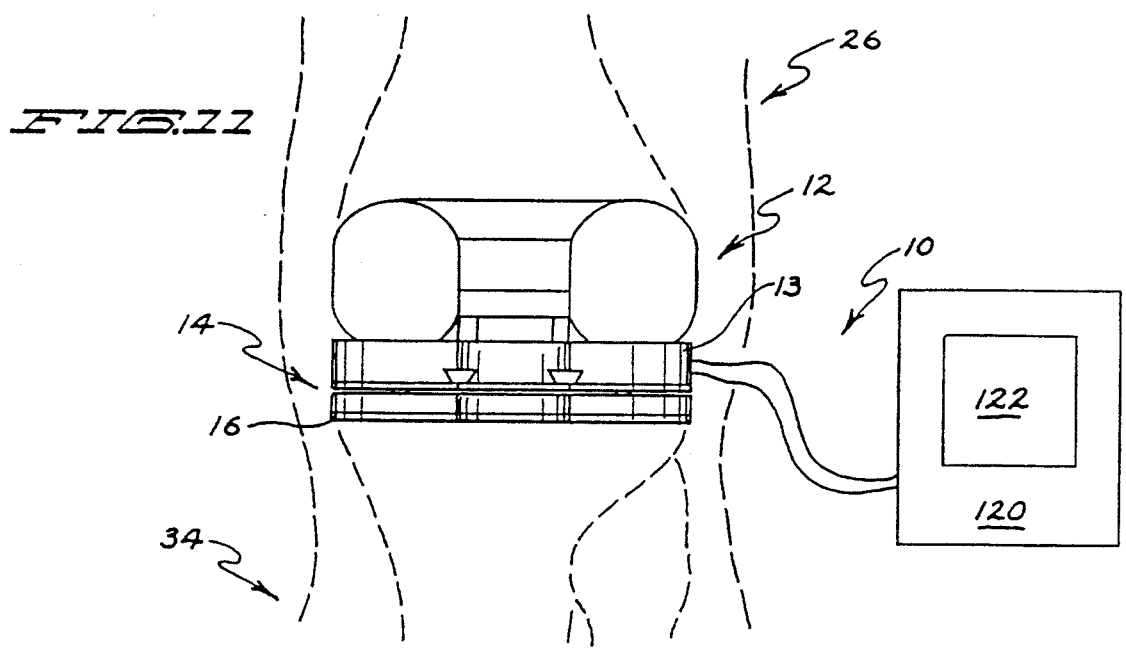
FIG. 11 is a front view of the knee prosthesis of FIG. 1 coupled schematically to a computer.
Figure 12:
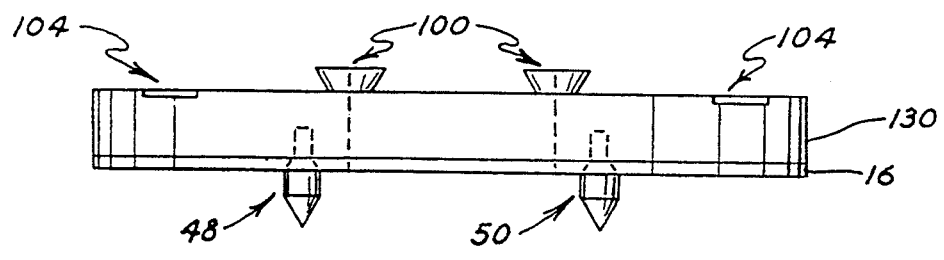
FIG. 12 is a front view of a spacer mounted on top of the cover plate.

In the preferred embodiment, assembly 10 further comprises a computer 120 electrically connected to transducer 14 as shown schematically in FIG. 11. Computer 120 includes a display 122 capable of presenting individual or combined measured forces applied to the transducer 14 in graphical, numerical or a combined format. Computer 120 stores the quantified data for documentation and analysis purposes. When proper alignment of the joint prosthesis is complete, based on force measurements obtained through transducer 14, transducer 14 is replaced with an appropriate spacer 130 shown in FIG. 12. Spacer 130 is equal in height to transducer 14 with the same general U-shape configuration. Identical dovetails 100, channels 104 and depressions 106 interlock spacer 130 with tibial platform 13. Like transducer 13, cover plate 16 connects to spacer 130 with threaded spikes 48 and 50. After cover plate 16 is affixed securely to the tibia plateau; the incisions are properly sutured; and the patient is taken to the recovery room.

In summary, the present invention provides an assembly and method for implantation of joint prostheses. The assembly measures forces present on the prosthesis in vivo as the joint is articulated through partial or complete range of movements. The resulting data is collected and analyzed to ensure proper force load distribution across the load bearing surfaces of the joint prosthesis. With proper load distribution, the joint prosthesis is optimally aligned thereby realizing increased prosthetic life.

Although the present invention has been described with reference to preferred embodiments, workers skilled in the art will recognize that changes may be made in form and detail without departing from the spirit and scope of the invention.

What is claimed is:

1. A transducer for measuring forces between two components of a joint prosthesis, the transducer comprising:
   a central body having a plurality of spaced apart integral flexure members forming an upper surface of the central body wherein each flexure member is formed by a corresponding cavity of a plurality of spaced apart cavities;
   a plate spaced apart from the upper surface;
   a plurality of support posts connecting the plate to the central body wherein each support post is located within the perimeter edge of the plate and has a first end attached to only one of the flexure members, and a second end attached to the plate, the support posts localizing forces applied to the plate onto the flexure members; and
   a force sensing element coupled to each flexure member, each force sensing element providing an output signal representative of the force applied to the corresponding flexure member.

2. The transducer as specified in claim 1 wherein each force sensing element comprises a strain gauge.

3. The transducer as specified in claim 2 wherein each strain gauge is resistive.

4. The transducer as specified in claim 1 wherein each support post is integrally connected to the plate and the corresponding flexure member.

5. The transducer as specified in claim 1 wherein each cavity is substantially cylindrical.

6. The transducer as specified in claim 5 wherein the plurality of cavities equals four.

7. The transducer as specified in claim 1 and a platform that is replaceably attached with locking means to an upper surface of the plate, the locking means aligning the platform on the plate and preventing both substantially perpendicular and lateral movement of the platform.

8. The transducer as specified in claim 7 wherein the locking means comprises a dovetail and notch interconnection to align the platform onto the plate and prevent substantial perpendicular movement of the platform from the plate.

9. The transducer as specified in claim 7 wherein the locking means comprises a depression termed in the upper surface of the plate and a protruding complementary element formed on a lower surface of the platform such that interaction of the protruding element with the depression prevents substantial lateral movement of the platform on the plate.

* * * * *

UNITED STATES PATENT AND TRADEMARK OFFICE
CERTIFICATE OF CORRECTION

PATENT NO. : 5,360,016

DATED : November 1, 1994

INVENTOR(S) : Nebojsa Kovacevic

It is certified that error appears in the above-indentified patent and that said Letters Patent is hereby corrected as shown below:

```
Column 8, line 22, delete "termed" and insert
--formed--.
```

Signed and Sealed this

Eleventh Day of April, 1995

BRUCE LEHMAN

*Attest:*

*Attesting Officer*    *Commissioner of Patents and Trademarks*

UNITED STATES PATENT AND TRADEMARK OFFICE
CERTIFICATE OF CORRECTION

PATENT NO. : 5,360,016
DATED : November 1, 1994
INVENTOR(S) : Nebojsa Kovacevic

It is certified that error appears in the above-indentified patent and that said Letters Patent is hereby corrected as shown below:

Column 7, line 19, after "attached" insert --directly--.

Signed and Sealed this

Sixth Day of June, 1995

Attest:

BRUCE LEHMAN

Attesting Officer     Commissioner of Patents and Trademarks